United States Patent
Ohmoto et al.

(10) Patent No.: US 7,009,714 B2
(45) Date of Patent: Mar. 7, 2006

(54) METHOD OF DRY ETCHING A SAMPLE AND DRY ETCHING SYSTEM

(75) Inventors: Yutaka Ohmoto, Hikari (JP); Ryouji Fukuyama, Kudamatsu (JP); Mamoru Yakushiji, Kudamatsu (JP)

(73) Assignee: Hitachi High-Technologies Corporation, Tokyo (JP)

( * ) Notice: Subject to any disclaimer, the term of this patent is extended or adjusted under 35 U.S.C. 154(b) by 332 days.

(21) Appl. No.: 10/372,838

(22) Filed: Feb. 26, 2003

(65) Prior Publication Data

US 2004/0165193 A1 Aug. 26, 2004

(51) Int. Cl.
*G01B 9/02* (2006.01)

(52) U.S. Cl. ..................................... 356/504
(58) Field of Classification Search ............... 356/496, 356/503, 504, 511
See application file for complete search history.

(56) References Cited

U.S. PATENT DOCUMENTS 5,440,141 A * 8/1995 Horie .................... 250/559.27
6,301,009 B1 * 10/2001 Tinker .................... 356/511
6,782,337 B1 * 8/2004 Wack et al. ............. 702/155

* cited by examiner

*Primary Examiner*—Gregory J. Toatley, Jr.
*Assistant Examiner*—Michael A. Lyons
(74) *Attorney, Agent, or Firm*—Antonelli, Terry, Stout and Kraus, LLP.

(57) ABSTRACT

A process recipe is controlled by processing reflection interference light on the surface of a wafer with a signal and etching is carried out by suppressing an increase in the surface roughness of the wafer during etching. That is, a dry etching method for use in a dry etching system comprising means of treating a sample by generating plasma in a vacuum process chamber and monitor means of monitoring the reflection interference light of the sample to be treated, the method comprising the step of detecting the spectrum of reflection interference light on the surface of the sample to be treated, the step of obtaining a residual from curve fit between a theoretical value estimated from the film reflection model of the surface of the wafer and the spectrum of reflection interference light, and the step of judging whether the residual from the curve fit falls within a predetermined value.

18 Claims, 8 Drawing Sheets

FIG. 5

| STATE OF CHAMBER \ USED RECIPE | STANDARD RECIPE (H₂/N₂=100/300 UHF=800W) | RECOVERY RECIPE 1 (H₂/N₂=120/300 UHF=800W) | RECOVERY RECIPE 2 (H₂/N₂=100/300 UHF=1000W) |
|---|---|---|---|
| STATE 1 | | | |
| STATE 2 | | | |

ELAPSED TIME FROM CLEANING OF CHAMBER →

WHEN THERE IS NO PORE

WHEN THERE IS A PORE

METHOD OF DRY ETCHING A SAMPLE AND DRY ETCHING SYSTEM

BACKGROUND OF THE INVENTION

1. Field of the Invention

The present invention relates to a method of plasma processing a sample such as a semiconductor integrated circuit and, particularly, to a dry etching method suitable for the treatment of an insulating film material having a low dielectric constant.

2. Related Background Art

Semiconductor integrated devices have a relatively larger electrostatic capacity between adjacent wirings in a wiring portion as the design rule is becoming narrower. When a conventional silicon oxide film is used as an insulating material between wirings, the benefit of increasing the speed of a transistor obtained by reducing the design rule cannot be obtained. Therefore, a material having a low dielectric constant (k value) is now used as an insulating material between wirings.

Since the above material is mainly used in combination with the copper of a wiring material and formed with means called "dual damascene", the step of etching the insulating material is necessary. This forming step using the dual damascene includes the substep of obtaining a predetermined form for a sample having a hole formed in the previous step by transferring a groove form to a porous insulating film using a hard mask. This technology is disclosed by Japanese Patent Laid-open No. H9(1997)-115878, for example.

Heretofore, when a process having a small margin due to a reduction in design rule is used, the reproduction stability of a treatment has been obtained by washing and cleaning a chamber periodically using a quality control technique. Also, the method of controlling the process by monitoring the state of the process has also been employed.

As the method of controlling the process by monitoring the state of the process is known a method in which etching is stopped by monitoring reflection interference light from the treated wafer as disclosed in U.S. Pat. No. 5,658,418.

However, process conditions required for a normal treatment are becoming more strict along with the narrowing design rule and further due to a specific phenomenon caused by porosity shown below. Materials having a low dielectric constant (k value) are now widely used due to a reduction in design rule and also materials having pores introduced therein called "porous insulating film" are used to further reduce the dielectric constant.

Further, a mask material is removed by using another vacuum vessel or other device in the same apparatus after the end of etching in the prior art. For example, Japanese Patent Laid-open No. 2000-352827 discloses a technology for removing the etching residue or a curing layer on the surface of a resist by a wet process.

Since a process having low tolerance and strict conditions is easily affected by the surface state of a chamber and the etched area of the treated wafer, the greatest care must be taken of the control of treatment reproducibility.

Particularly, in the etching of a porous insulating film, the influence of the geometrical structure of a pore appears though the structure is fine. The case where there is a pore and the case where there is no pore are compared conceptually with reference to FIGS. 12A and 12B when the pore is seen microscopically. When there is no pore in the material, as shown in FIG. 12A, the angle α between an ion having a certain incident angle and the etched surface 122 of a material 120 is the same, for example, 90° at different positions S1 and S2 on the horizontal plane as a matter of course. On the other hand, when there is a pore 124 in the material 120, as shown in FIG. 12B, the angle α between the ion and the etched surface 122 at a position S1 may differ from the angle α at a different position S2 on the horizontal plane. Meanwhile, ions having different incident angles may differ in etching rate. Thereby, the influence of the pore appears in the material having the pore 124 in an exaggerated manner.

Seeing the scale of a pattern for processing this, as shown in FIG. 13, when a groove is to be formed in a porous insulating film 120 on a base film 134 by etching using a hard mask 130, the surface having a groove form is roughened 132 during etching and grows. Finally, a plurality of residues 140 as shown in FIG. 14 remain in the bottom of the etched groove.

The residues 140 cause an embedding failure during the subsequent step of metal deposition and cannot be removed by cleaning. Therefore, they must be completely removed in the etching step. It is possible to reduce the amount of the residues to a certain extent by increasing the over-etching time. However, the shoulder portion of the hard mask is easily chipped off by increasing the over-etching time, thereby causing a reduction in yield such as a short-circuit between wirings. An increase in over-etching time also causes the etching of the base film 134 and a dimensional error. Therefore, countermeasures must be taken in the etching step.

To achieve a treatment without the residues and the high-accuracy transfer of a pattern at the same time, neutral deposition and etching radicals are well balanced. However, the external controllability of neutral radicals does not reach a required level and a quality control technique must be introduced. That is, a method of actually processing a test wafer at a cycle at which safety can be expected by statistically acquiring information on influencing changes and confirming the process is necessary.

However, control frequency and the number of wafers to be confirmed are increased by a further reduction in tolerance due to a reduction in design rule, thereby boosting cost.

SUMMARY OF THE INVENTION

It is an object of the present invention to provide a method of dry etching a sample and a dry etching system, capable of effecting a stable treatment when a film having a low dielectric constant used in a dual damascene is etched and eliminating an increase in cost.

It is another object of the present invention to provide a method of dry etching a sample and a dry etching system, capable of effecting a stable treatment when a sample, especially a porous insulating film is etched and eliminating an increase in cost.

In the present invention, the process recipe is controlled by processing reflection interference light on the surface of a wafer with a signal and etching is carried out by suppressing an increase in the surface roughness of the wafer during etching.

More specifically, the present invention is a dry etching method for use in a dry etching system comprising means of processing a sample by generating plasma in a vacuum process chamber and monitor means for monitoring the reflection interference light of the sample to be treated, the method comprising the step of detecting the spectrum of reflection interference light on the surface of the sample to be treated, the step of obtaining a residual from the curve fit between the spectrum of the reflection interference light and a theoretical value estimated from the film reflection model of the surface of a wafer, and the step of judging whether the residual from the curve fit falls within a predetermined range.

According to the present invention, the residual from the fit obtained from comparison between the intensity spectrum of interference reflection light from the surface of the wafer and the intensity spectrum of interference reflection light estimated from the film structure of the surface of the wafer is monitored so that the processing method is changed by the value of the residual from the fit or a time change in the value.

To suppress the surface roughness during etching, the dependence upon ion incident angle of the etching rate which is the cause of surface roughness may be reduced. However, this increases the etching rate of ions incident obliquely to the surface which must be treated vertically, which may lead to a treatment failure such as side etching.

In the present invention, a plurality of process recipes in which neutral and non-directional deposition radicals and etching radicals are well balanced are constructed, and the operation recipe is changed by monitoring the surface state of the wafer, thereby making it possible to obtain a good treated form without the residue. As a result, an insulating film having a low dielectric constant is etched stably at a low product quality control cost.

According to the present invention, the plasma treatment of a sample, particularly an insulating film having a low dielectric constant can be carried out stably at a low product quality control cost.

BRIEF DESCRIPTION OF DRAWINGS

FIG. 5 is a diagram showing treatment results obtained from the state of a chamber and the used recipe in the embodiment of FIG. 1;

DESCRIPTION OF THE PREFERRED EMBODIMENTS

Figure 1:
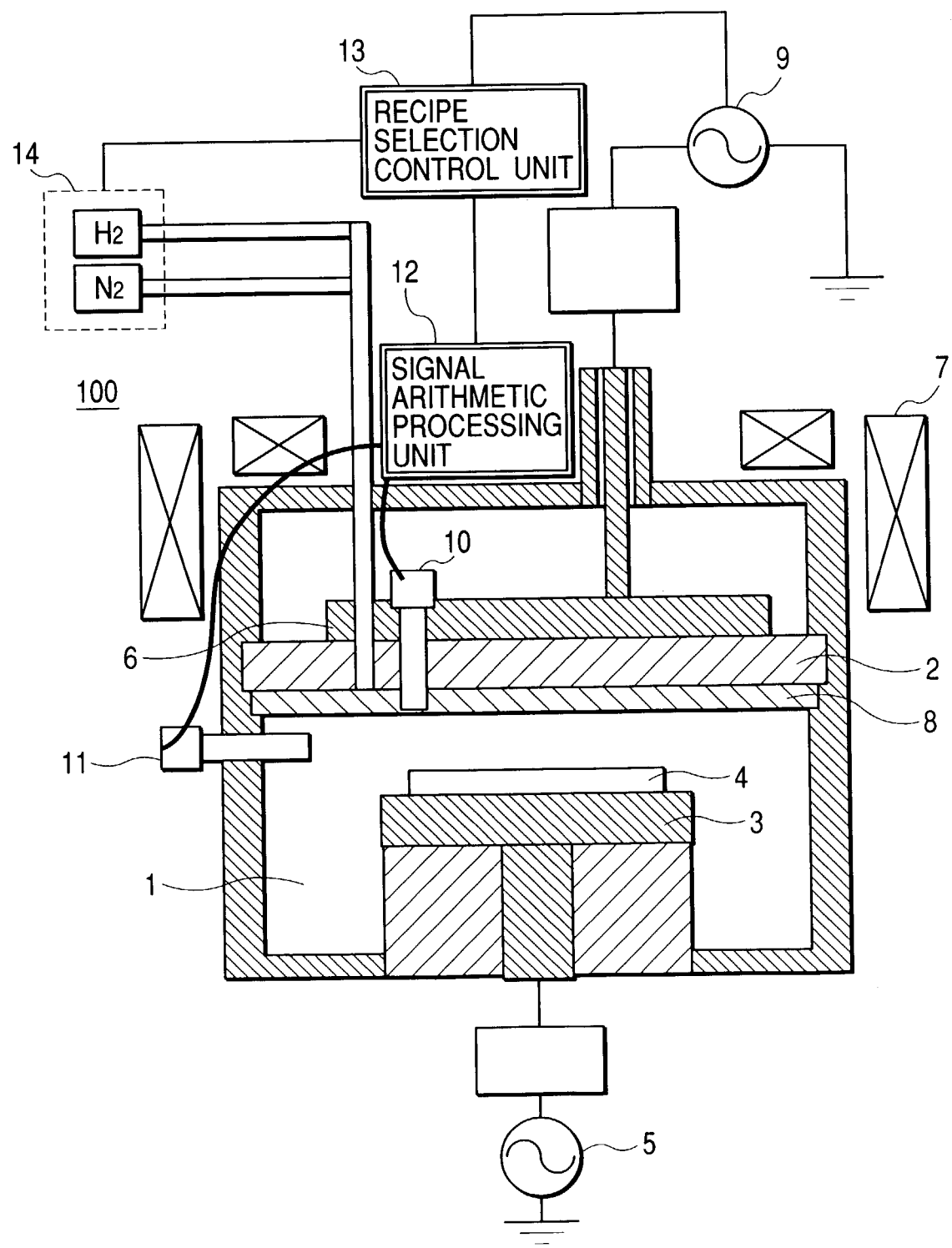
FIG. 1 is a structural sectional view of a vacuum treatment system used in one embodiment of the present invention.

A preferred embodiment of the present invention will be described hereinbelow with reference to an example in which a UHF-ECR vacuum treatment system is used. FIG. 1 is a schematic sectional view of the vacuum treatment system to which an embodiment of the present invention is applied. The vacuum treatment system 100 comprises a plurality of vacuum process chambers (plasma chambers) 1, vacuum conveyance chamber and a pair of lock chambers. The vacuum treatment system 100 is an ECR type vacuum treatment system which generates plasma by interaction between electromagnetic waves radiated from an antenna and a magnetic field. An aluminum antenna 6 and a quartz window 2 are mounted on the top of each vacuum process chamber 1 to pass a UHF electromagnetic field into the vacuum process chamber 1. The antenna 6 is connected to a UHF power source 9 for generating UHF electromagnetic waves having a frequency of 450 MHz through a coaxial wave guide or matching transformer. A solenoid coil 7 is wound round the vacuum process chamber 1 to form a magnetic field in the vacuum process chamber 1.

A lower electrode 3 for mounting a wafer 4 as a sample having a semiconductor integrated circuit is placed in the vacuum process chamber 1. The interval between a quartz window 2 and the lower electrode 3 is adjusted to 30 to 100 mm. The space between the quartz window 2 and the lower electrode 30 is a treatment space into which plasma is generated.

The lower electrode 3 is connected to a high-frequency bias power source 5 for providing incident energy upon the wafer 4 to ions contained in the plasma and to an ESC power source (not shown) for electrostatically chucking the wafer 4 to the lower electrode 3. The frequency of the high-frequency bias power source 5 is not particularly limited but a frequency of 200 kHz to 20 MHz is generally used. An exhaust port is formed in the bottom of the vacuum process chamber 1 and an unshown exhaust system is connected to the exhaust port.

Reference numeral 10 denotes a reflection light intensity monitor for monitoring a time change in the intensity of reflection light of plasmas light from the surface of the wafer 4 at a wavelength range of 300 to 800 nm. Denoted by 11 is a plasma light monitor for monitoring plasma light by avoiding reflection light from the surface of the wafer. The outputs of the monitors 10 and 11 are processed by an arithmetic processing unit 12 in accordance with a predetermined method. The arithmetic processing unit 12 controls a series of processes for processing the wafer in the vacuum treatment system. Numeral 14 denotes a controller for a gas feeder for feeding processing gas into the vacuum process chamber 1. Gas supplied from the mass flow controller 14 according to etching recipe is uniformly introduced into the vacuum process chamber 1 through a gas dispersion board 8. A recipe selection control unit 13 controls the output power of the UHF power source 9 and the flow rate of the mass flow controller 14 based on a predetermined recipe. The control system including the arithmetic processing unit 12 carries out arithmetic processing required for judging the selection of a recipe and outputs its result to the recipe selection control unit 13.

On the lock chamber side of the vacuum treatment system 100, an atmosphere conveyor having a transport robot and further a cassette table which can mount a plurality of cassettes are placed. An inspection device is provided to the atmosphere conveyor and the vacuum treatment system 100. The measurement results of the inspection devices are input into the control system so that the etching condition control unit of the control system adjusts the processing conditions of the wafer in the vacuum process chamber based on the measurement results.

The control system is composed of a computer having a CPU, memory, program, external memory and input/output means and controls the vacuum treatment system 100. The inspection devices measure an increase (CD gain) in the width of a processing line from a design value by means of a measurement SEM. This measurement is carried out on one wafer at a time or a predetermined number of wafers at a time, and the measurement data are stored in the memory of the control system. A predetermined permissible range is set for the CD gain, and initial etching conditions, that is, etching conditions at the start of lot treatment are set to ensure that this CD gain falls within this permissible range. Wafers are treated continuously. When the CD gain exceeds the permissible range, this data signal is transmitted to an etching condition adjusting unit in the control system so that the etching condition adjusting unit automatically adjusts the conditions to ensure that the CD gain falls within the permissible range and the control system changes or adjusts the etching conditions in the vacuum process chamber of the vacuum treatment system. The inspection devices inspect the treated wafers one by one to check the existence of the residue and judges whether the wafers are acceptable or not. Wafers unacceptable due to the existence of a large amount of the residue by the inspection are removed and not transmitted to the subsequent processing step. On the other hand, inspection information on wafers accepted by this inspection is reflected on the subsequent processing step. For example, correction processing is made on a wafer which has been accepted by inspection but has a relatively large amount of the residue in consideration of the residue in the subsequent step.

The input/output means of the control system has a display unit for displaying the existence of the residue, the result of inspection, the current operation recipe and the like for each wafer.

A description is subsequently given of the processing contents of the arithmetic processing unit 12 and the recipe selection control unit 13 with reference to FIGS. 2 to 5.

Figure 2:
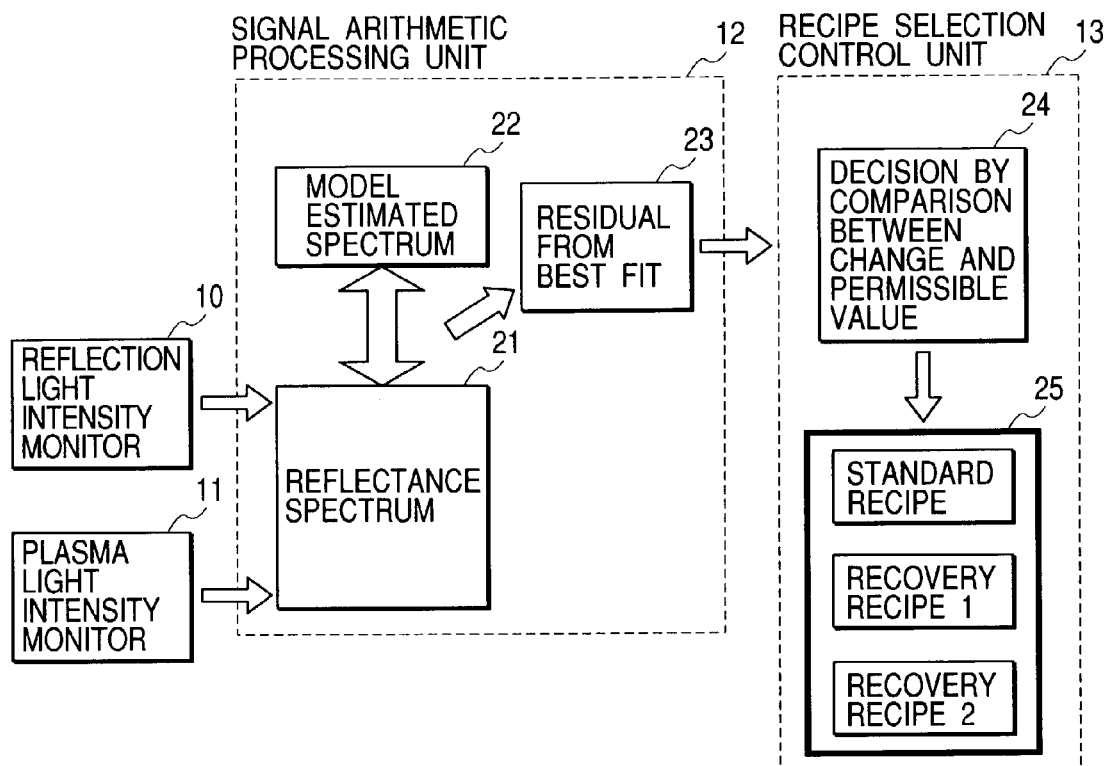
FIG. 2 is a block diagram of the extraction of a residual from the fit and the control of recipe selection in the embodiment of FIG. 1.

FIG. 2 is a functional block diagram of the arithmetic processing unit 12 and the recipe selection control unit 13. In FIG. 2, the arithmetic processing unit 12 obtains data on the standard recipe for operating the vacuum process chamber from the recipe selection control unit 13 to control a series of processes for treating the wafer in the vacuum process chamber 1. The wafer 4 is etched with the standard recipe using plasma in the vacuum process chamber 1. Plasma light for the treatment of the wafer 4 and reflected light are monitored and the monitored data are transmitted to the plasma light arithmetic processing unit 12. In the plasma light arithmetic processing unit 12, a reflectance spectrum computing unit 21 normalizes a signal from the reflection light intensity monitor 10 with a signal from the plasma light intensity monitor 11 to compute the actually measured reflectance spectrum at a plurality of wavelengths. Meanwhile, a model estimate spectrum computing unit 22 computes a model estimated spectrum from the already known film structure model of a wafer.

Figure 3:
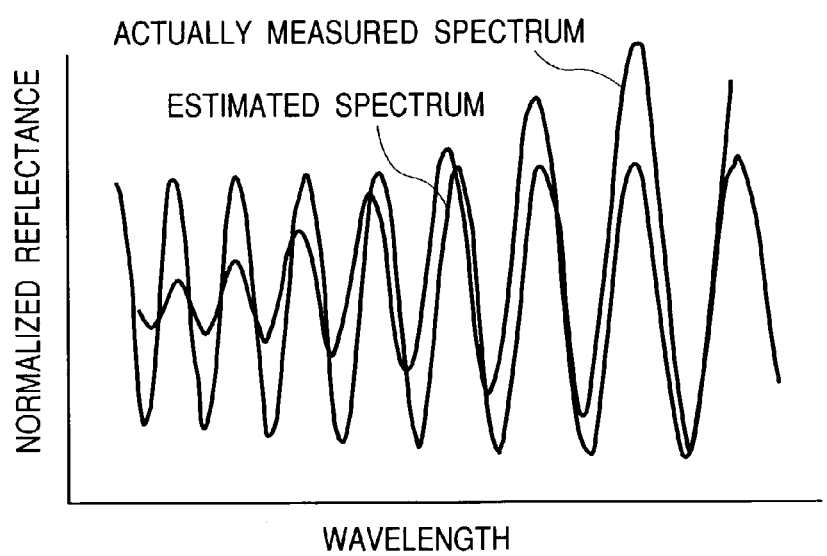
FIG. 3 is a diagram showing the relationship between the actually measured spectrum of reflectance and the estimated spectrum of reflectance in the embodiment of FIG. 1.

FIG. 3 shows an example of the relationship between the normalized reflectance of the actually measured reflectance spectrum and the normalized reflectance of the model estimated spectrum estimated from the film structure model of the wafer.

Subsequently, a fitting processing unit 23 carries out fitting processing to match the actually measured reflectance spectrum with the model estimated spectrum.

A residual (residual D from the fit) between the spectra after fitting so that these spectra are best matched is output to the recipe selection control unit 13 and its absolute value or time change is compared with a set value by a comparison decision unit 24. Based on this result, it is judged whether the selection of a recipe should be changed or not. That is, the chamber state of the wall or the like of the vacuum process chamber 1 is estimated from the above absolute value or time change value and it is judged whether the change falls within a permissible range.

Figure 4A:
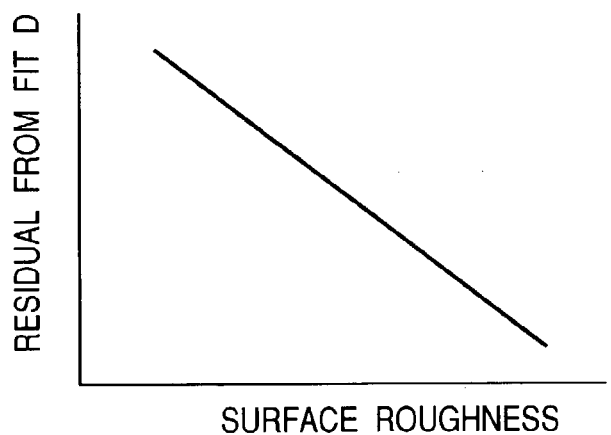
FIG. 4A is a diagram showing relation between the above residual D from the fit and the surface roughness of the treated sample.
Figure 4B:
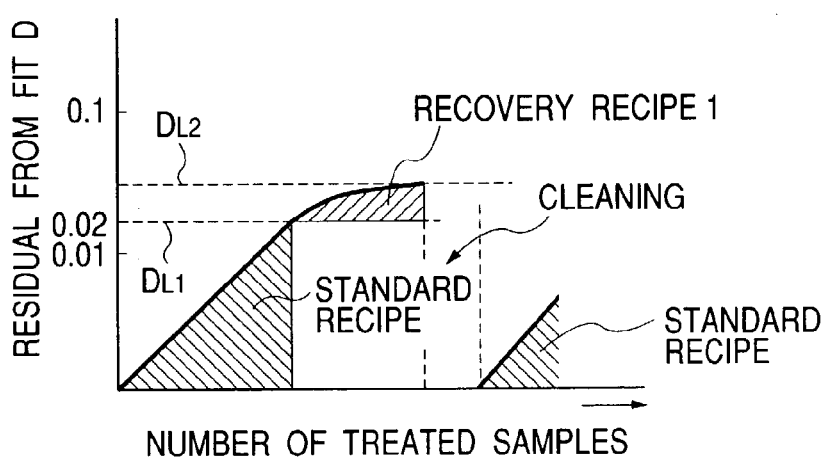
FIGS. 4B to 4C are time charts of a residual from the fit and a used recipe in the embodiment of FIG. 1.
Figure 4C:
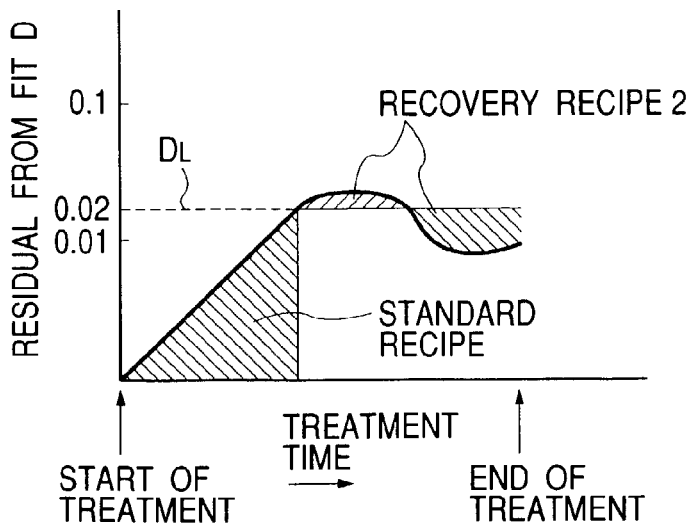

FIG. 4A is a diagram showing relation between the above residual D from the fit and the surface roughness of the treated sample, and FIGS. 4B to 4C are time charts of a residual from the fit and the used recipe.

As shown in FIG. 4A, the above residual D from the fit and the surface roughness of the treated sample are substantially in inverse proportion to each other.

FIG. 4B shows that when the residual D from the fit is a first permissible value DL1 or less, the vacuum process chamber is operated with the standard recipe, and when the residual D from the fit is larger than the first permissible value DL1 and a second permissible value DL2 or less, the vacuum process chamber is operated with a recovery recipe 1. When the residual D from the fit is larger than the second permissible value DL2, the vacuum process chamber is cleaned and then operated with the standard recipe again.

FIG. 4C shows that when the residual D from the fit is the first permissible value DL1 or less, the vacuum process chamber is operated with the standard recipe, and when the residual D from the fit is larger than the first permissible value DL1 and the second permissible value DL2 or less, the vacuum process chamber is operated with a recovery recipe 2. The recovery recipe 2 is an operation recipe having the function of cleaning the vacuum process chamber.

Thus, when the absolute value or change value of the residual D from the fit is larger than the permissible value DL, an appropriate recipe stored in the recipe selection unit 25 is selected to change the processing conditions for treating the wafer in the vacuum process chamber 1 from the standard recipe to the recovery recipe 1 or 2.

A description is subsequently given of a plurality of recipes stored in the recipe selection unit 25.

(a) standard recipe: H2/N2=100/300 power for generating plasma (UHF)=800 W
(b) recovery recipe 1: 20% increase of the flow rate of H2
(c) recovery recipe 2: 25% increase of power (UHF)

The recovery recipes 1 and 2 are for increasing the unidirectional etching rate and has a tendency toward side etching compared with the standard recipe 1. Thus, a process in which neutral and non-directional deposition and etching radicals are slightly well balanced is constructed.

The treatment process of the wafer 4 is easily shifted by the influence of the surface state of the vacuum process chamber 1 and the influence of the etched area of the wafer. Therefore, the greatest care must be taken of the control of treatment reproducibility.

FIG. 5 shows the mutual relationship between the two states of the vacuum process chamber and the treated form of the sample when three different recipes are used.

In general, the sample can be etched into a normal form without the residue using the standard recipe 1 in the chamber state 1 which is relatively clean after the cleaning of the vacuum process chamber 1. That is, when etching is carried out with the "standard recipe" while the vacuum process chamber 1 is in "state 1", for example, a state where it can be operated under normal conditions without the adhesion of foreign matter on the inner wall like the state right after cleaning, the form of the groove in the surface of the sample becomes normal.

When etching is carried out with the "standard recipe" while the vacuum process chamber 1 is in "state 2" where foreign matter is adhered to the inner wall of the vacuum process chamber 1 after the etching of a plurality of samples, the residue remains in the groove in the surface of each sample. However, when etching is carried out with "recovery recipe 1" or "recovery recipe 2" while the vacuum treatment 1 is in "state 2", the residue is removed and the form of the groove in the surface of the sample becomes normal.

However, when the recovery recipe 1 or recovery recipe 2 is used in the chamber state 1, side etching is seen though there is no residue. This readily causes an embedding failure in the subsequent step.

Meanwhile, when the standard recipe is used in the chamber state 2 after etching is carried out several times after cleaning, the residue is produced by keeping using the standard recipe but normal etching can be carried out by using the recovery recipe 1 or 2.

When the residual is outside the predetermined range and the effect of reducing the residue is not observed even by using the recovery recipe 1 or 2 continuously, it is recommended to stop etching the wafer 4 for avoiding failures and clean the vacuum process chamber 1.

Figure 6:
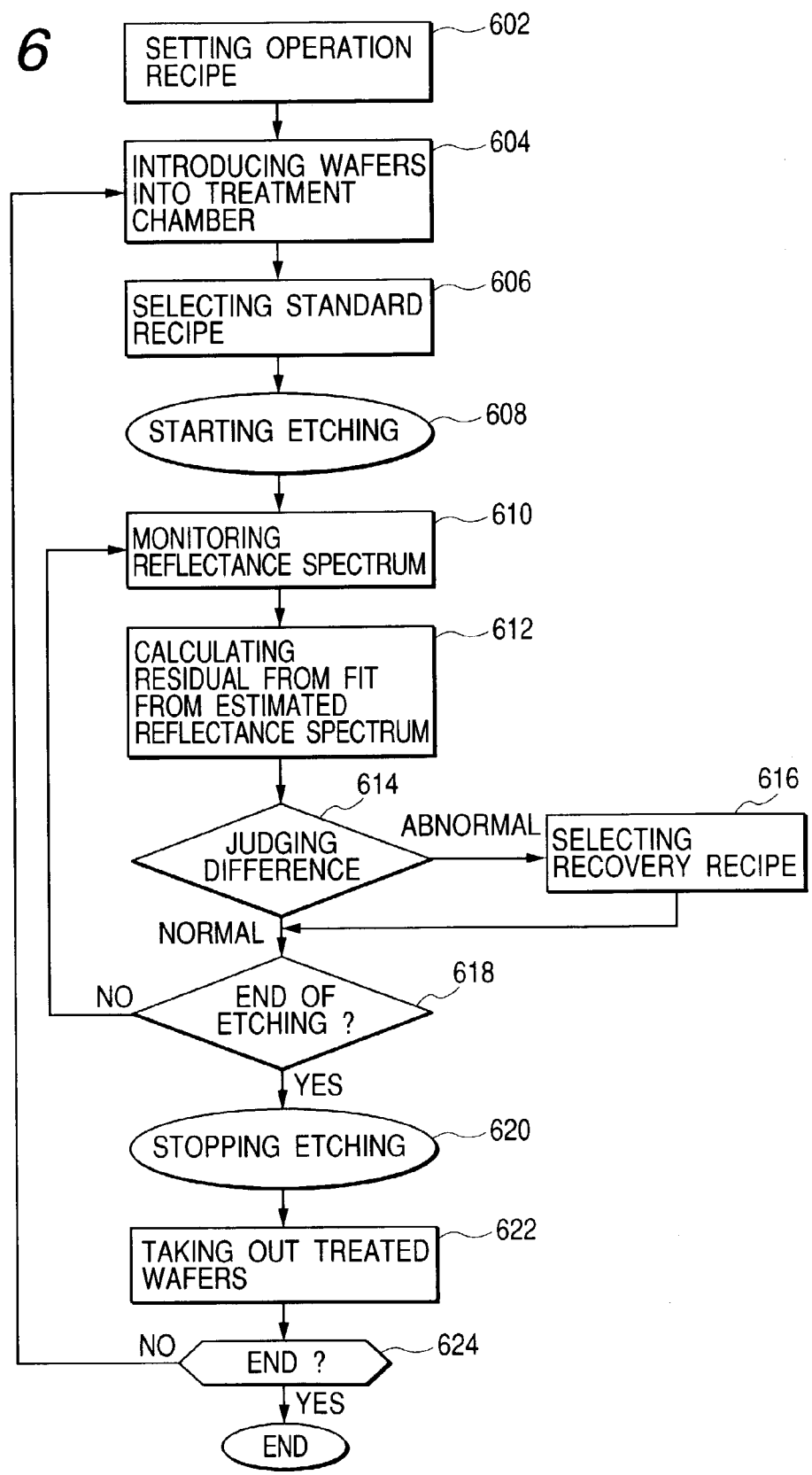
FIG. 6 is a flow chart of process control in the embodiment of FIG. 1.

FIG. 6 shows a flow chart of a treatment in the embodiment of the present invention. First, an operation recipe for the etching process of the wafer 4 is suitably set (602). Then, after the wafer is introduced into the treatment chamber (604) etching is started with the standard recipe (606 to 608). The arithmetic processing unit 12 monitors the residual from the fit during etching and outputs its result at all times to judge the residual D (610–614).

When it is judged that the surface of the wafer is roughened and the residual from the fit becomes large, it is considered that the chamber state has been changed, the recovery 1 or 2 is accordingly selected (616), etching is carried out to the end point, and then the wafer is carried after etching. Etching of the next wafer is started with the standard recipe, when the residual from the fit becomes large, the recovery recipe 1 or 2 is selected, and etching is carried out to the end point (618). The similar treatment is repeated for all the wafers to be treated under the same conditions (604–624).

Figures 7A, 7B, 7C:
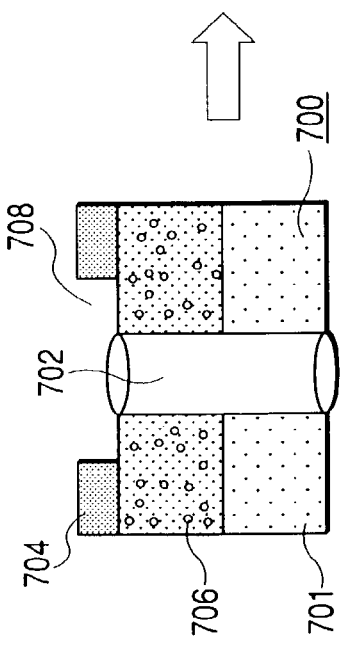
FIG. 7 is a diagram for explaining the etching process of a sample in the embodiment of FIG. 1.

FIG. 7 illustrates part of the step of forming with a dual damascene which the present invention is directed to. As described above, materials having a low dielectric constant (k value) are now widely used and also materials having pores introduced therein called "porous insulating film" are used to further reduce the dielectric constant. Since the above materials are mainly used in combination with the copper of a wiring material and formed by means called "dual damascene", the step of etching the insulating material is necessary. That is, as shown in FIG. 7A, a groove 708 is transferred to the porous insulating film 706 of a sample 700 having a hole 702 formed in the previous step using a hard mask 704. Numeral 701 denotes a base insulating film.

In the etching of the porous insulating film, the influence of the fine geometrical structure of the pore appears and the surface is roughened 730 during etching as shown in FIG. 7B. Therefore, etching must be carried out by suppressing an increase in the surface roughness during etching. To suppress the surface roughness 730 during etching, the dependence upon ion incident angle of the etching rate which is the cause of the roughened surface may be reduced. The recovery recipes 1 and 2 are intended to increase the isotropic etching rate and have a tendency toward side etching. Thus, a process in which neutral and non-directional deposition and etching radicals are well balanced is constructed.

Therefore, when it is judged that the residual from the fit becomes large due to the roughened surface of the wafer, the recovery recipe 1 or 2 is selected to etch the water to the end point.

Thus, the good treated form 740 of the groove without the residue as shown in FIG. 7C can be obtained.

According to the present invention, even in the case of the treatment having a small process margin of a porous insulating film, the on-the-spot detection of surface roughness which causes the production of the residue and the control of changing the recipe in order to prevent a failure caused by the residue are possible and further the control of changing the state of the vacuum process chamber is also possible. As a result, a semiconductor integrated circuit can be produced at a low cost.

Examples of the present invention will be described with reference to FIGS. 8 to 11.

EXAMPLE 1

First, as an example of the present invention, 50 wafers having the same mask pattern and an organic porous insulating film having a dielectric constant of 2.2 were etched using the UHF-ECR type vacuum treatment system shown in FIG. 1. When the treated wafers were inspected, first to 27-th wafers passed a residue failure test but 28-th and subsequent wafers did not pass the test.

Figure 8:
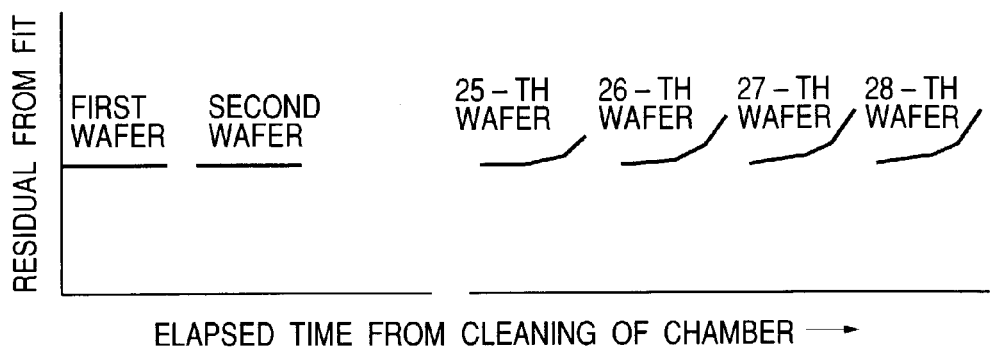
FIG. 8 is a diagram showing changes in residual from the fit when a residue failure occurs.

Data continuously sampled and recorded by the monitors 10 and 11 were processed and analyzed by the signal arithmetic processing unit 12. As a result of analysis, the fitting coefficient began to change from the estimated value of a film thickness model in the latter half stage of the etching step of the 25-th wafer as shown in FIG. 8, the change became larger gradually in the subsequent wafers and the treatment was repeated while the width of the change was saturated.

EXAMPLE 2

Figure 9:
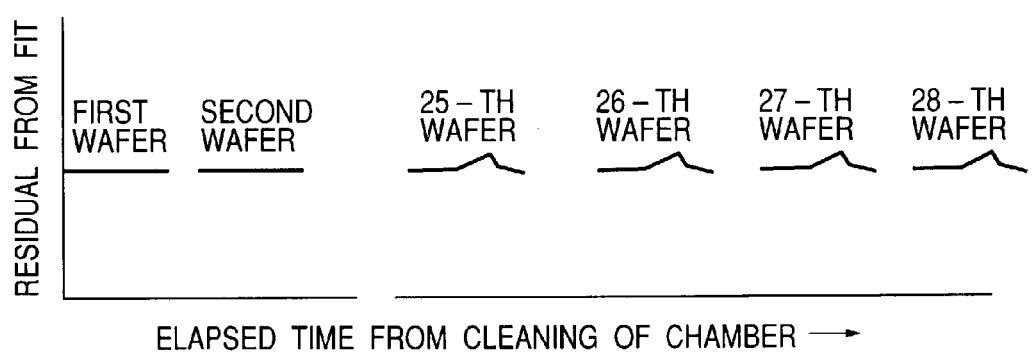
FIG. 9 is a diagram for explaining the effect of Example 1 of the present invention with changes in residual from the fit.

As another example of the present invention, when a change from the fitting value was detected, control was carried out using the recovery recipe 1 in which the flow rate of an etching gas was increased by a predetermined amount in place of the standard recipe to process 50 samples of the same type continuously as described above. As a result, as shown in FIG. 9, the recovery control did not work on first to 24-th wafers. However, recovery control worked from the 25-th wafer that etching was carried out with a recipe in which the flow rate of the gas was increased. After the recovery control worked on the 25-th and subsequent wafers, the fitting coefficient D was gradually improved and returned to a value smaller than the permissible value DL before the start of etching at the end of etching.

When the residue failure test was made on the 50 wafers which were continuously treated, all the wafers passed the test that the amount of the residue was below the specified value DL.

EXAMPLE 3

Figure 10:
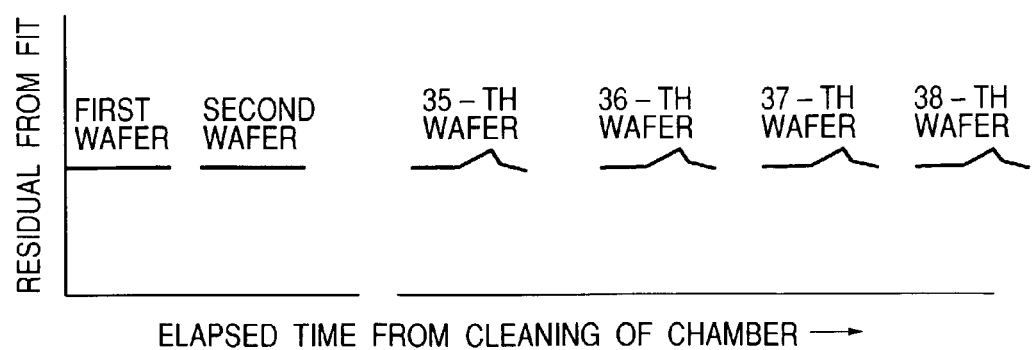
FIG. 10 is a diagram for explaining the effect of Example 2 of the present invention with changes in residual from the fit.
Figure 11:
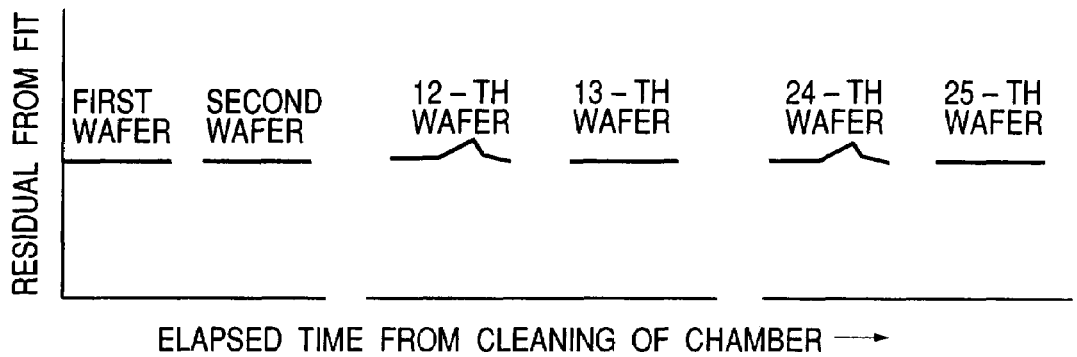
FIG. 11 is a diagram for explaining the effect of Example 3 of the present invention with changes in residual from the fit.
Figure 12A:
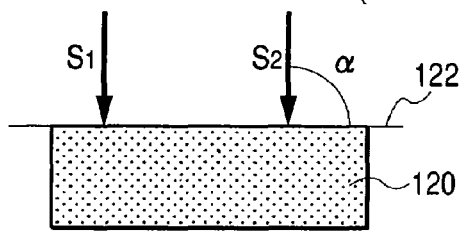
FIGS. 12A and 12B are diagrams for explaining that etching becomes different according to the existence of a pore.
Figure 12B:
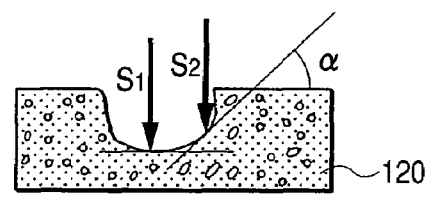
Figure 13:
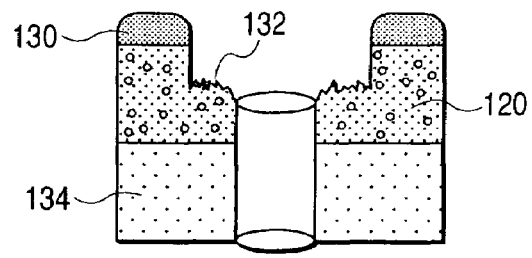
FIG. 13 is a diagram for explaining surface roughness during etching.
Figure 14:
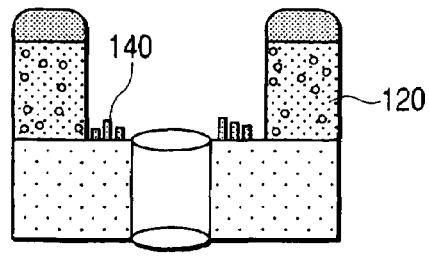
FIG. 14 is a diagram for explaining the production of the residue after etching.

As still another example of the present invention, 50 samples having a different mask pattern as the above samples were etched with the recovery recipe 1 by the control method of the present invention. In this case, as shown in FIG. 10, use of the recovery recipe started from the 35-th wafer to the final 50-th wafer. When the existence of the residue and size were inspected for the 50 treated wafers, all the wafers came up to the standard and were accepted.

Thereafter, the recovery recipe 2 in which UHF power as plasma generation power was increased from that of the standard recipe was used as the recovery recipe. Using this recovery recipe 2 and the control method of the present invention, 50 samples were continuously treated. In this case, as shown in FIG. 10, control worked on 12-th, 24-th, 36-th and 48-th samples periodically. Similarly, when the existence of the residue and size were inspected for the 50 samples, they all came up to the standard. The reason why the control worked intermittently unlike the previous examples seems to be that not only the surface of the wafer but also the state of the chamber were returned to the initial states after cleaning by the recovery recipe 2 for increasing UHF power.

As obvious from these examples, according to the present invention, quality control work which costs dear is not necessary and fine semiconductor integrated circuits can be produced at a high yield.

Although the reflected light of plasma light is used as the reflected light of a wafer in examples of the present invention, a plurality of different light sources may be used to utilize their reflected light, which is within the scope of the present invention. The vacuum process chamber is not limited to a UHF-ECR type and a vacuum process chamber of a different type may be used.

According to the present invention, the plasma treatment of a sample, especially an insulating film having a low dielectric constant can be carried out stably with a low product quality control cost.

What is claimed is:

1. A method of dry etching a sample with a dry etching system comprising means of treating a sample by generating a plasma in a vacuum process chamber and monitor means of monitoring the reflection interference light of the sample to be treated, the method comprising the steps of:
    etching the sample using plasma in the vacuum process chamber;
    monitoring light of the plasma for etching the sample and reflected light of the plasma on a surface of the sample to be treated;
    detecting the spectrum of reflection interference light;
    obtaining a residual from curve fit between a theoretical value estimated from the film reflection model of the surface of the sample and the spectrum of the reflection interference light;
    judging whether the residual from the curve fit falls within a predetermined range; and
    changing the method of treating the sample when the residual is outside the predetermined range.

2. The dry etching method of claim 1, wherein when the residual is outside the predetermined range, the method of treating the sample is changed.

3. The dry etching method of claim 1, wherein the change of the sample treating method includes the change of power for generating plasma.

4. The dry etching method of claim 1, wherein the change of the sample treating method includes the change of the flow rate of treating gas for generating plasma.

5. The dry etching method of claim 1, wherein when the residual is outside the predetermined range, the treatment of the sample is stopped.

6. The dry etching method of claim 1, wherein the step of detecting the spectrum of reflection interference light includes normalizing a signal of the monitored reflected light with a signal of the monitored plasma light.

7. A dry etching method comprising the steps of:
    etching the sample using plasma in a vacuum process chamber;
    monitoring light of the plasma for etching the sample and reflected light of the plasma on a surface of the sample to be treated;
    detecting the intensity spectrum of reflection interference light;
    monitoring a residual from fit by comparing the intensity spectrum of interference reflection light on the surface of the sample with the intensity spectrum of interference reflection light estimated from the film structure of the surface of the sample;
    signal processing reflection interference light with the monitor value or a time change in the monitor value; and
    changing the method of treating the sample during etching based on the result of the signal processing to suppress an increase in the surface roughness of the sample.

8. The dry etching method of claim 1 or 7, wherein neutral and non-directional deposition and etching radicals are well balanced to control the surface roughness of the sample to a predetermined range.

9. The dry etching method of claim 1 or 7 comprising the step of displaying whether the surface roughness of the sample falls within a predetermined range and the change of the method of treating the sample on a display unit.

10. The dry etching method of claim 1 or 7, wherein when the residual is in the predetermined range, it is corrected in the subsequent step of a dry etching system using information on the residual.

11. The dry etching method of claim 1 or 7, wherein the treatment of the sample is the etching of an insulating film having pores therein.

12. The dry etching method of claim 7, wherein the step of detecting the spectrum of reflection interference light includes normalizing a signal of the monitored reflected light with a signal of the monitored plasma light.

13. A dry etching system comprising means of treating a sample by generating plasma in a vacuum process chamber and monitor means of monitoring the reflection interference light of the sample to be treated, wherein
    the system further comprises a unit for monitoring light of the plasma for etching the sample and reflected light of the plasma on a surface of the sample to be treated while etching the sample using the plasma in the vacuum process chamber; a unit for detecting the intensity spectrum of reflection interference light on the surface of the sample to be treated, a unit for obtaining a residual from curve fit between the spectrum of reflection interference light and a theoretical value estimated from the film reflection model of the surface of the sample, and means of judging whether the residual from the curve fit falls within a predetermined range.

14. The dry etching system of claim 13, which further comprises a unit changing the method of treating the sample when the residual is outside the predetermined range.

15. The dry etching system of claim 14, wherein the unit for changing the method of treating the sample includes means for obtaining information on a plurality of operation recipes having different etching conditions and means of outputting any one of the operation recipes.

16. The dry etching system of claim 13, wherein the unit for obtaining a residual from curve fit between a theoretical value estimated from the film reflection model of the surface of the sample and the spectrum of reflection interference light includes means of normalizing a signal from a reflection light intensity monitor with a signal from a plasma light intensity monitor to calculate the actually measured spectrum of reflectance at a plurality of wavelengths and means of carrying out a fitting treatment so that the actually measured spectrum of reflectance agrees with a model estimated spectrum.

17. The dry etching system of claim 13 which comprises a display unit for displaying the result of judgment on whether the residual from the curve fit falls within a predetermined range and the change of the method of treating the sample.

18. The dry etching system of claim 13, wherein the unit for monitoring plasma light and reflected light includes a plasma light intensity monitor providing an output signal and a reflection light intensity monitor providing an output signal, and wherein the unit for detecting the intensity spectrum of reflection interference light includes means for normalizing the output signal of the reflection light intensity monitor with the output signal of the plasma light intensity monitor.

* * * * *